United States Patent [19]

Hofelich et al.

[11] Patent Number: 4,957,707
[45] Date of Patent: Sep. 18, 1990

[54] THERMAL HAZARD EVALUATION

[75] Inventors: Thomas C. Hofelich, Midland; Michael S. LaBean, Auburn, both of Mich.

[73] Assignee: The Dow Chemical Company, Midland, Mich.

[21] Appl. No.: 238,889

[22] Filed: Aug. 31, 1988

[51] Int. Cl.$^5$ ............................................. B01L 3/00
[52] U.S. Cl. ..................................... 422/102; 422/51; 436/174; 374/31; 206/219
[58] Field of Search .................. 422/51, 102; 436/174, 436/180, 147; 206/219-222; 366/242; 604/82, 83, 85; 374/31

[56] References Cited

U.S. PATENT DOCUMENTS

| | | |
|---|---|---|
| 3,193,357 | 7/1965 | Benzinger . |
| 3,417,972 | 12/1968 | Vincent ............................. 366/242 |
| 3,449,081 | 6/1969 | Hughes . |
| 3,877,877 | 4/1975 | Prosen . |
| 4,130,016 | 12/1978 | Walker ............................. 422/51 |
| 4,152,117 | 5/1979 | Böhm ............................. 422/51 |
| 4,379,775 | 4/1983 | Brandstetr et al. ............................. 422/51 |
| 4,772,031 | 9/1988 | Poppo ............................. 206/219 |
| 4,779,763 | 10/1988 | Klawitter ............................. 206/219 |

Primary Examiner—Robert J. Warden
Assistant Examiner—D. John Griffith, Jr.
Attorney, Agent, or Firm—John K. McCulloch; Burke M. Halldorson

[57] ABSTRACT

A disposable mixing cell and method for evaluating the thermal hazard due to mixing substances includes a first container adapted for the accommodation of a sample of one substance and a second container in the form of a syringe adapted to accommodate a sample of a second substance. The syringe is operable to discharge the second substance into the substance in the first container and includes a paddle by means of which the two substances may be mixed. The syringe is sealed within the first container, except for the outer end of its operating plunger which is accessible externally of the first container. The mixing cell is placed in a batch type fluid calorimeter which is capable of indicating the thermal reaction resulting from the mixing of the two substances. A gas conduit may be provided to conduct gas evolved from the mixing of the two substances outward of the cell.

11 Claims, 2 Drawing Sheets

THERMAL HAZARD EVALUATION

This invention relates to a mixing cell and method for use in evaluating hazardous reactions resulting from the mixing of different substances.

BACKGROUND OF THE INVENTION

One of the most common problems encountered in an industrial environment is that of determining the reactive compatiblity of two or more substances when they are mixed. The necessity of determining such compatibility arises when waste materials are mixed for or during disposal, during absorption of accidentally spilled materials, or in the formulation of a chemical product. The problems inherent in mixing substances of these kinds have been recognized heretofore and a number of techniques proposed for their solutions.

In one of the prior art techniques differential scanning calorimetry (DSC) or differential thermal analysis (DTA) is used to detect potentially hazardous interactions in a mixture of a number of individual components. One of the problems with this procedure is that a reaction may occur as a result of mixing which cannot be detected using either of the DSC or DTA techniques. For example, the DSC curves of solutions of aqueous NaOH and HCl appear unchanged from the resulting NaCl solution formed upon their mixing, yet the reaction resulting from the mixing can produce enough heat to boil the resultant water in those instances in which concentrations of the reactants are sufficiently great. Typically, this problem has been circumvented by establishing estimates of heats of mixing by the use of a Dewar flask fitted with a thermocouple or thermometer. Volumes used in such a test typically range from 10 mL up to 150 mL.

Another procedure for use in assessing potential hazards resulting from binary mixtures is an adiabatic mixing test. This test involves a three-step method including the measurement of the adibatic temperature rise of a 1:1 molar mixture of the materials in an open Dewar flask. A measurement of the pressure change upon mixing of such materials observed to react below 46° C. also was made in a sealed Dewar flask or instrumented Parr bomb (for the most reactive materials). Finally, those materials observed not to react upon initial mixing were subjected to DTA.

The adiabatic mixing test has been attractive because it involves a total approach of determination of the reaction upon mixing, as well as the higher temperature thermal stabilities. In addition, pressure measurements are of considerable significance in the evaluation of the overall potential hazard. It has been observed, however, that the experimental temperature rises increase as the volumes used in the tests increase. This is due to the relatively large changes in heat losses of the reaction vessel system as the volumes of the materials are increased. Although the observed temperature rises in small-scale tests approach those of a large-scale process as the volumes increase, safety risks increase when larger quantities of materials are used in the tests for obtaining more accurate data relating to temperature rises.

Another prior art technique utilizes an accelerating rate calorimeter (ARC). In this technique one of the materials is present in the bomb and another material is introduced to the bomb via a syringe having a long, small gauge dispensing needle. The temperature in the ARC then is increased to detect any potentially hazardous reactions. Although this technique is sound, it is lengthy and expensive to perform. Typical ARC tests require as long as eight to ten hours to complete. Further, serious errors can arise from the temperature mismatch of the added material. For example, 2 mL of aqueous material at 23° C. added to the bomb at 30° C. yielded a 14 caloric decrease. This endothermic heat can partially mask exothermic reaction.

An object of the present invention is to provide an apparatus and method for assessing the hazard of mixing materials and which overcome the problems associated with the prior art methods and apparatus.

SUMMARY OF THE INVENTION

A mixing cell constructed according to the invention comprises a first container such as a transparent test tube in which a small sample of one substance may be introduced. A second container, such as a syringe, has a transparent barrel within which is a small sample of a second substance. The syringe includes a dispensing needle through which the second substance sample may be ejected into the first container for mixing with the first substance sample. Preferably, the needle has fitted thereto a paddle by means of which the first and second substances may be mixed.

The syringe is mounted and supported in the first container by means of a septum formed of resilient, flexible material. The syringe has a plunger which extends through the septum so as to be externally accessible for dispensing the contents of the syringe into the first container. The flexibility and resilience of the septum enable the syringe to be manipulated in such manner that the paddle can stir and mix the two samples.

The mixing cell, composed of the assembled first and second containers, is accommodated in a batch calorimeter having conventional means associated therewith for responding to and recording thermal reactions resulting from the mixing of the two samples.

A flexible tube may extend from the interior of the first container through the septum to conduct gas from the first container to a burette of known construction which is used in a conventional manner to analyze gas produced by the mixing of the two samples.

The materials used for the construction of the mixing cell are readily available and are so inexpensive that the cell may be disposable, thereby avoiding the cleaning and other costs and disadvantages associated with conventional apparatus in use for similar purposes.

The time required to evaluate the thermal hazard resulting from the mixing of samples of two substances is a small fraction of the time heretofore required for similar purposes.

THE DRAWINGS

FIG. 1 is a vertical sectional view of a mixing cell constructed and assembled in accordance with the invention and in condition to mix two substances for thermal hazard evaluation; and FIG. 2 is a vertical sectional view, on a reduced scale, illustrating the mixing cell accommodated in a batch calorimeter.

DETAILED DESCRIPTION

Figure 1:
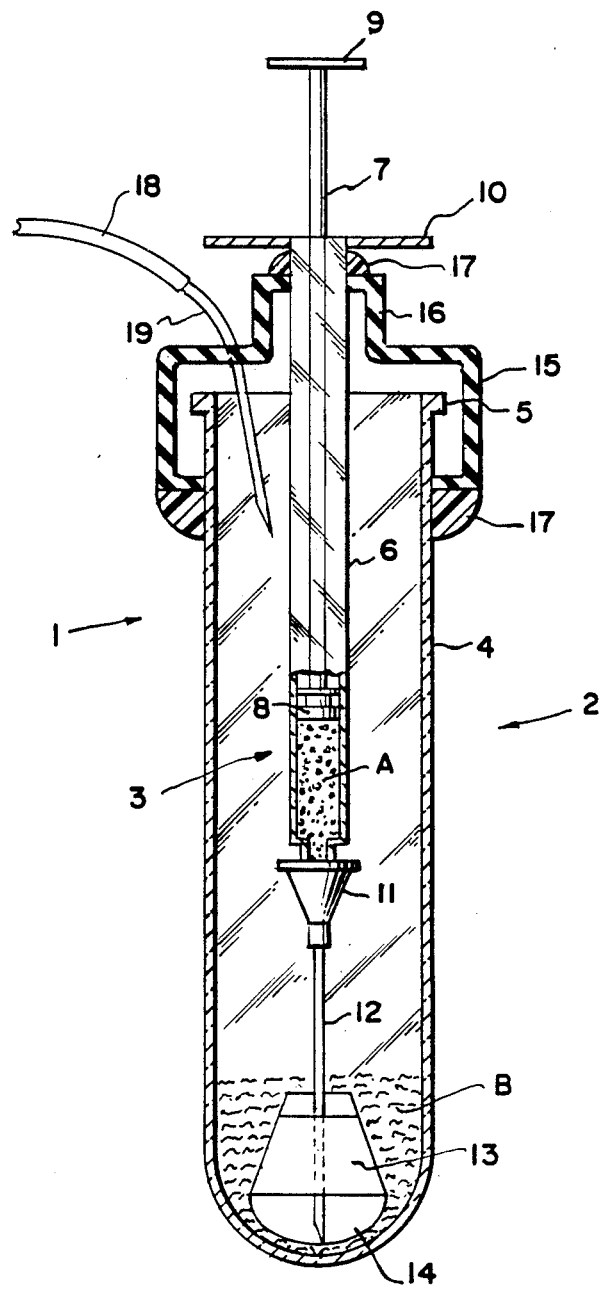

A thermal hazard evaluation mixing cell constructed in accordance with the invention is designated generally by the reference character 1 and comprises a first container 2 for the accommodation of a sample of one substance and a second container 3 for the accommodation of a sample of a second substance that is to be mixed with the first sample. The first container 2 comprises a transparent test tube 4 formed of glass or other suitable material having good thermal conductivity. The container is closed at one end and terminates at its other end in an opening encircled by a bead or rim 5. The second container 3 preferably comprises a conventional syringe having a graduated glass or synthetic material barrel 6 within which is a reciprocable operating plunger 7 provided at one end with a piston 8 and at its opposite end with a finger piece 9. Fitted to one end of the barrel 6 is a conventional flange 10. At the opposite end of the barrel is a nozzle 11 in which is secured one end of a dispensing needle or conduit 12 formed of stainless steel or other suitable stiff material and through which the contents of the syringe may be ejected. The needle is fitted to a flat paddle 13 formed of an inert material such as polytetraflouroethylene. The tip 14 of the paddle preferably is shaped to conform substantially to the closed end of the test tube 4.

The syringe is removably mounted in the container 2 by a resilient, flexible septum 15 formed of rubber or other inert rubbery sealing material. Adjacent the open end of the test tube the septum has an upstanding cap 16 which encircles the barrel 6 of the syringe and forms a gas tight seal for the open end of the test tube. The natural seal provided by the rubbery septum may be enhanced by a paraffin tape 17 applied to the exterior of the septum and the adjacent parts of the containers 2 and 3 so as to ensure that neither of the samples inadvertently can escape its container.

To condition the cell for use, the plunger 7 is withdrawn from the barrel 6 of the syringe and a measured quantity, such as 1 mL, of one of the substances to be mixed is introduced to the barrel. The plunger then is replaced. The substance introduced to the syringe is a fluid medium indicated by the reference character A. A measured quantity, such as 1 mL, of a second substance indicated by the reference character B is introduced to the container 2. The substance B may be either a fluid or a solid. If solid, however, the substance B preferably is particulate in form so as to facilitate mixing.

Following the introduction of the samples of the substances A and B to their respective containers, the syringe (previously having been fitted to the septum 15 via an opening therein) is introduced to the container 2 through its open end, following which the paraffin tape 17 is fitted to the respective containers. A hollow tube 18, formed of inert material such as that mentioned above, then may be inserted into the container 2 so as to conduct gas from the latter. One end of the tube 18 is provided with a hollow needle 19 by means of which the tube may pierce the septum 15. The other end of the tube may be inserted in a water-filled, inverted burette (not shown) whose tip has been sealed, as is conventional, and which is held suspended in a dish that also is filled with water.

Figure 2:
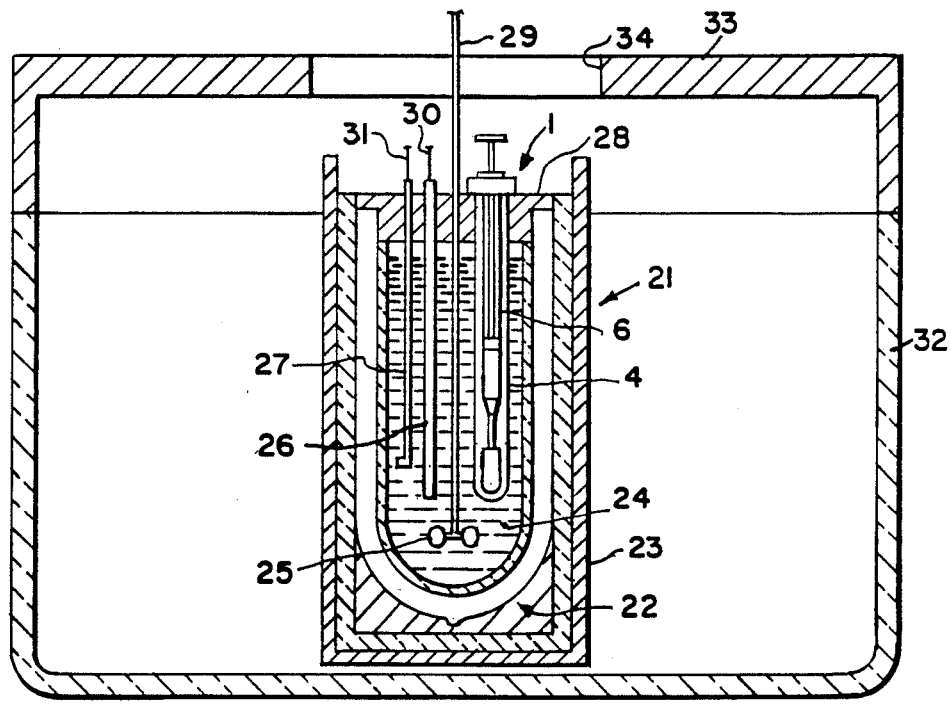

Following preparation of the mixing cell 1 for use, it may be placed in an isoperibol batch calorimeter 21 shown in FIG. 2, or in any other appropriate commercially available calorimeter such as a Parr model 1451 solution calorimeter, suitably modified for accommodation of the cell 1.

The calorimeter 21 includes a Dewar flask 22 accommodated in an insulated, brass jacket 23. The flask 22 contains a sufficient quantity of fluid 24, such as water, to ensure good heat transfer between such fluid and the cell. Immersed in the fluid is a stirrer 25, a heating element 26, and a thermistor 27. The flask is fitted with a cap 28 formed of inert material through which the cell 1, an operating rod 29 for the stirrer, and leads 30 and 31 from the heater and thermistor project. The flask 22 and its jacket 23 are placed in an insulated housing 32 having a removable cover 33 and containing a fluid such as air. The cover has an opening 34 to provide access to the calorimeter.

In a typical test, the substances A and B are placed in their respective containers and the cell 1 placed in the calorimeter 21 as shown. The gas tube 18 (if provided) is connected to its burette and the leads from the heater and thermistor are connected to their sources of energy and measuring devices, respectively, in a conventional manner. The calorimeter 21 is coupled in a conventional manner to a strip chart recorder of known kind.

After placing of the mixing cell and the calorimeter in the housing, the system is permitted to reach thermal equilibrium. Upon reaching thermal equilibrium, after a few minutes time the contents A of the syringe 3 are ejected via the nozzle 11 and the needle 12 into the container 2 onto the substance B. Preferably the substance B is agitated by the paddle 13 as the substance A is added thereto. In this connection, the resilience and flexibility of the material forming the septum 15 enables racking movements of the syringe manually to effect agitation and mixing of the substances A and B via the paddle 11. The transparency of the test tube 4 enables the results of mixing of the substances A and B to be inspected without removal of the mixture from the container 4, if desired.

Heat generated by the mixing of the substances A and B will be transferred from the cell 1 to the calorimeter fluid 24 via the wall of the test tube 4. Data generated from such transfer of heat are delivered to the recorder and monitored in the conventional manner, and such data may be used in known manner to calculate the heat of mixing of the substances A and B. Since good heat transfer is maintained between the cell and the calorimeter fluid, temperature rise in the cell is kept to a minimum.

What is claimed is:

1. A mixing cell adapted for use in testing the reaction resulting from the mixing of different substances, said cell comprising a first container open at one end and closed at its other end for accommodating a sample of one substance; a second container for accommodating a sample of another substance, said second container occupying a position in which at least a portion thereof is accommodated within said first container; flexible and resilient means rockably mounting said second container in said position and forming a seal for the open end of said first container; operating means in communication with said second container and accessible from outside both of said containers for discharging a substance from said second container onto a substance in said first container; and agitating means carried by said second container adjacent said other end of said first container and engageable with a substance in said first container for agitating such substance in response to rocking movement of said second container relative to said first container.

2. A mixing cell according to claim 1 including tubular gas conduit means sealingly supported by said mounting means in communication with said first container for conducting gas from the interior of said first container to its exterior.

3. The mixing cell according to claim 1 wherein said operating means comprises a plunger fitted into said second container for expelling a substance in said second container through an opening therein.

4. The mixing cell according to claim 3 including a nozzle in communication with said opening for conducting a substance expelled through said opening into said first container.

5. The mixing cell according to claim 4 wherein said agitating means is carried by said nozzle.

6. A mixing cell adapted for use in testing the reaction resulting from the mixing of different substances, said cell comprising a tubular container formed of thermally conductive material for accommodating one substance, said container being closed at one end and open at its opposite end; a syringe having a barrel and a plunger, said barrel being adapted to accommodate another substance; flexible and resilient means mounting said syringe at least partially within said container for rocking movements relative thereto and sealing the open end of said container, said plunger extending through said mounting means and being accessible externally of said container for discharging a substance in said barrel into said container for mixing with a substance therein; and agitating means carried by said syringe and extending into said container adjacent its close end, said agitating means being responsive to rocking movements of said syringe relative to said container to mix substances in said container.

7. The mixing cell according to claim 6 including tubular gas conduit means sealingly supported by said mounting means in communication with said container for conducting gas from the interior of said container to its exterior.

8. The mixing cell according to claim 6 including an elongate, stiff, hollow dispenser carried by said syringe and through which a substance in said barrel may be expelled by said plunger.

9. The mixing cell according to claim 8 wherein said agitating means is carried by said dispenser for mixing the contents of said container.

10. The mixing cell according to claim 9 wherein said agitating means comprises a flat paddle fitted to said dispenser.

11. The mixing cell according to claim 10 wherein said dispenser comprises a needle which extends through said paddle.

* * * * *